United States Patent [19]

Ankeny et al.

[11] Patent Number: 5,299,140

[45] Date of Patent: Mar. 29, 1994

[54] MEANS AND METHOD FOR MEASUREMENT OF POROUS MATERIALS

[75] Inventors: Mark D. Ankeny; Mark Burkhard, both of Albuquerque, N. Mex.

[73] Assignee: Daniel B. Stephens & Associates, Inc., Albuquerque, N. Mex.

[21] Appl. No.: 902,386

[22] Filed: Jun. 23, 1992

[51] Int. Cl.$^5$ .............................................. G01N 13/00
[52] U.S. Cl. ........................................ 364/497; 73/38; 364/550; 364/556
[58] Field of Search .................... 73/38; 364/497, 550, 364/556

[56] References Cited

U.S. PATENT DOCUMENTS 3,882,714  5/1975  Libal et al. ................................ 73/38
4,920,792  5/1990  DiFoggio ................................ 73/153

Primary Examiner—Edward R. Cosimano
Attorney, Agent, or Firm—Zarley, McKee, Thomte, Voorhees & Sease

[57] ABSTRACT

An apparatus and method for determining physical and chemical properties of a porous medium such as soil or rock. A sample of porous medium is held within a container. Conditions regarding the sample are sensed, including but not limited to weight, temperature, pressure, and humidity. Conditions at the sample can be brought to equilibrium or varied according to instructions. A control system can adjust or equilibrate the conditions according to desire and according to which properties or relationships between physical and chemical properties are desired to be derived.

37 Claims, 2 Drawing Sheets

VALVE CONFIGURATION NOTES

ENERGIZED        DE-ENERGIZED

```
L---FLOW DIRECTIONS---J
```

N.O.=NORMALLY OPEN VALVE PORT
    (CLOSES WHEN VALVE IS ACTUATED)

N.C.=NORMALLY CLOSED VALVE PORT
    (OPENS WHEN VALVE IS ACTUATED)

IN =INLET VALVE PORT
    (ALWAYS OPEN)

MEANS AND METHOD FOR MEASUREMENT OF POROUS MATERIALS

BACKGROUND OF THE INVENTION a. Field of the Invention

The present invention relates to measurement of physical and chemical properties of porous materials such as soil and rocks; and in particular, to a means and method for concurrently determining several of such properties.

b. Problems in the Art

A number of physical and chemical properties of porous media or materials are of interest. For example, the water content, permeability, specific surface area, and other properties and parameters associated with soil are important in analyzing soil and how it will react to certain conditions.

Furthermore, the relationships between various physical and chemical properties is also important in such an analysis. For example, water content - water potential relationships (and hysteresis in such relationships) can provide valuable information about soil.

There are currently a variety of ways to obtain these types of properties and parameters, and relationships between different properties and parameters. Normally, an experimental set up is utilized to obtain each one. It is therefore somewhat difficult to obtain a number of different properties because many times one must use different experimental set ups for different properties. It is difficult to move from one to the next; taking time and resources to do so.

It is also difficult to establish and derive quick and accurate measurements of the properties. Furthermore, the same difficulties occur when deriving relationships between the properties.

Still further, it is difficult to test how changes in properties may effect other properties. There is therefore a real need in the art for an improvement in this area.

The need exists for a more comprehensive measurement system. Such a system ideally would allow at least some of the following:

1. Measurement of a number of conditions or parameters concurrently;
2. Measurement and derivation of a number of relationships between conditions or parameters;
3. Variability of conditions or parameters allow evaluation of the effect of variations of conditions on other conditions or relationships;
4. A single integrated system for accomplishing these steps;
5. Flexibility of measurement and control; and
6. Automation and centralization for collection, control, calculation, and recordation of measurements and analysis.

It is therefore a principle object of the present invention to provide a means and method for measuring porous media which improves over the state of the art.

Another object of the present invention is to provide a means and method as above described which is integrated in one system.

Another object of the present invention is to provide a means and method as above described which can concurrently measure not only individual conditions or parameters of the porous medium, but also relationships between conditions or parameters.

Still further object of the present invention is to provide a means and method as above described which allows better sample preparation for measurement.

Another object of the present invention is to provide a means and method as above described which provides improved precision and results of measurements.

Another object of the present invention is to provide a means and method as above described which allows flexible and precise control.

Another object of the present invention is to provide a means and method as above described which allows accurate equilibrium of the system.

Still further of the present invention is to provide a means and method as above described which provides for better and more measurements of conditions and relationships related to the porous medium.

SUMMARY OF THE INVENTION

The present invention includes a means and method to facilitate improved measurements of physical and chemical properties and relationships between properties of a porous medium such as soil or rock. The means according to the invention utilizes a sample holder which is communicated with a fluid circuit. A pump means provides air flow through the circuit. Air flow can be selectively directed in either direction through the sample.

Appropriate components allow pressure in the circuit to be increased or decreased. Additionally, the circuit allows selective communication to either a humidifying means or a dehumidifying means to change humidity in the circuit and sample.

Measurement components and sensors are utilized to measure such conditions as flow through the sample, pressure at the sample, temperature at the sample, and humidity. A control means can be utilized to control the conditions at the sample and obtain data from the measurement components and sensors. The control means can then, according to programming, maintain certain conditions, vary certain conditions, or equilibrate the system according to certain instructed guidelines.

The method of the invention includes steps of simultaneously creating conditions at the sample related to flow, humidity, pressure, and temperature. Measurements are then taken of these conditions. Physical and chemical properties of the sample can then be evaluated and relationships between those properties derived to evaluate the sample.

DETAILED DESCRIPTION OF PREFERRED EMBODIMENT

Figure 1:
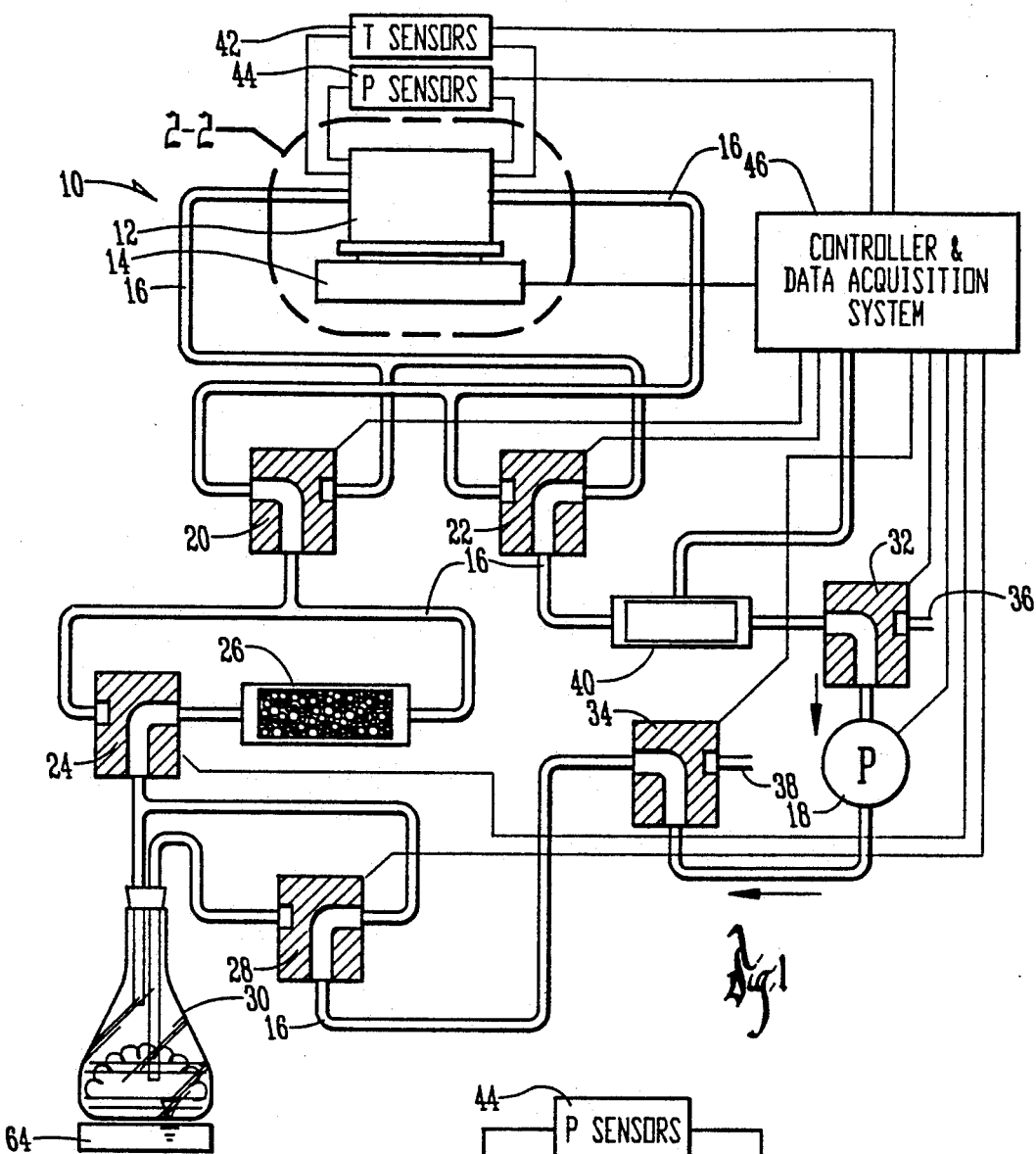
FIG. 1 is a schematic view of an apparatus according to the present invention.

To assist in a better understanding of the invention, a preferred embodiment of the invention will now be described in detail. Reference will be taken to the appended drawings. Reference numerals will be utilized in the drawings to indicate specific parts and locations in the drawings. The same reference numerals will be used throughout the drawings for the same parts and locations unless otherwise indicated.

It is to be understood that this is a preferred embodiment only and does not show all possible ways the invention can be utilized; and does not discuss all possible ways in which the method can be accomplished.

a. Structure of FIG. 1

FIG. 1 shows a combination of components according to the present invention. This will be called vapor equilibrium system 10 for purposes of this discussion. System 10 allows concurrent measurement of physical and chemical properties and relationships between properties for a porous media such as soil or rock. Operation of the system will be described in greater detail later.

In FIG. 1, system 10 is comprised of a sample holding cell 12 which is mounted on a standard laboratory balance 14. Tubing 16, which forms a circuit through a variety of other components, is connected to opposite left and right sides of cell 12.

As can be appreciated, cell 12 can be made air tight and has structure which can hold a sample so that air flow through the sample will be totally through the sample and not through any gaps or channels around the sample.

A peristaltic pump 18 is positioned along tubing 16. It is to be understood that pump 18 can be any positive displacement pumping mechanism compatible with this system 10. Pump 18 serves to produce an air flow through tubing 16 in the direction shown by the arrows immediately before and after pump 18.

A number of valves are shown in the circuit of tubing 16. These valves allow for control of fluid through the pathways of the circuit. For example, valves 20 and 22 cooperate with the tubing 16 as shown in FIG. 1, to either allow air flow in a right to left direction through cell 12 (which is the situation shown in FIG. 1) or in left to right direction through cell 12 (which would occur if valves 20 and 22 were reversed in position).

Valve 24 controls whether air flow will be through desiccator 26, or whether it will bypass desiccator 26. Likewise valve 28 determines whether air flow will be through wetting flask 30; o whether it will bypass wetting flask 30. Valves 24 and 28 therefore can either completely bypass desiccator 26 and wetting flask 30, select one or the other, or select both. Normally one or the other of desiccator 26 and wetting flask 30 will be selected or neither.

Finally, valves 32 and 34 operate to either put the circuit of tubing 16 in communication with vents 36 and 38 (which are to atmosphere), or seal tubing 16 off from vents 36 and 38. It is to be understood that normally valve 32 will be opened to atmosphere if more intake air is needed by pump 18 to increase pressure in the circuitry of tubing 16, and valve 34 is opened to vent or exhaust air to atmosphere, if pressure within the circuit of tubing 16 is desired to be decreased. Therefore, valves 32 and 34 either operate both closed from vents 36 or 38; or one only is open to a vent 36 or 38.

FIG. 1 also shows a humidity and temperature measurement chamber 40 is inserted in tubing 16 between valves 22 and 32. Chamber 40, such as is known in the art, is used to measure the humidity and temperature in the circuit of tubing 16. FIG. 1 also shows that temperature sensors 42 and pressure sensors 44 are connected to cell 12 and measure temperature, absolute pressure and relative pressure of the interior of cell 12.

Controller and data acquisition system 46 is, in the preferred embodiment, a computing means that operates according to software programming. It receives input from temperature and pressure sensors 42 and 44, humidity and temperature measurement cell 40, and balance 14 to measure parameters or conditions existing with respect to the sample and the system circuit. It also issues instructions to valves 20, 22, 24, 28, 32, 34, and pump 18, to control flow of fluid through tubing 16.

Figure 3:
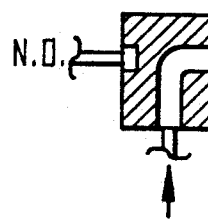
FIG. 3 is a legend illustrating the valve configuration conventions for FIG. 1.
Figure 3:
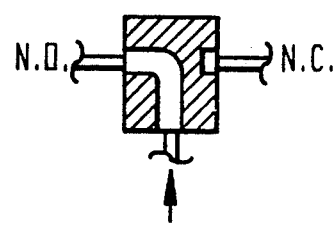

The legend of FIG. 3 depicts the valve configuration for the valves of the preferred embodiment of FIG. 1. Valves in FIG. 1 are 3-way solenoid valves and are shown in various states of energization and de-energization, as will be further described later in this description.

b. Structure of FIG. 2

Figure 2:
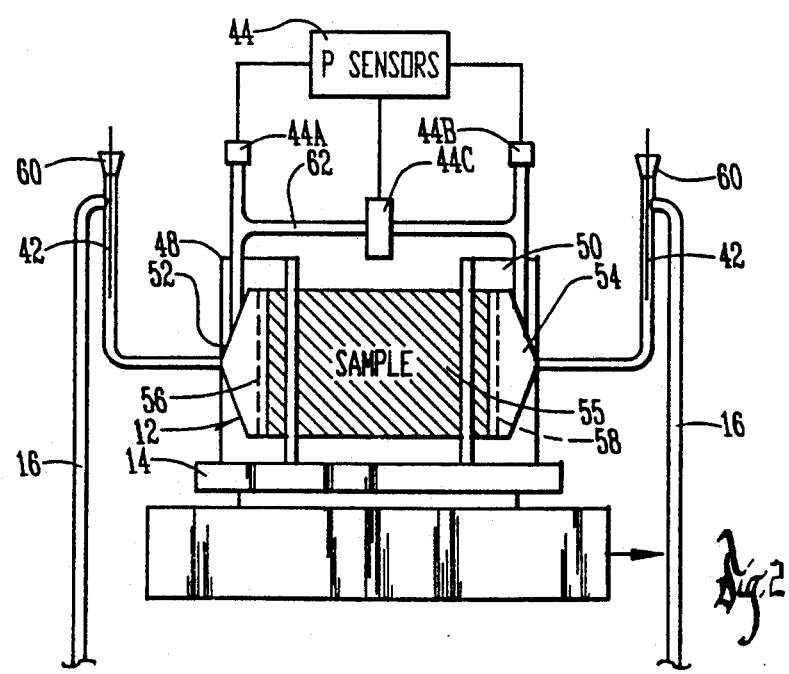
FIG. 2 is an enlarged front elevational view of the portion of the embodiment of FIG. 1 as shown by line 2—2 in FIG. 1.

FIG. 2 shows in more detail the structure of cell 12 and its associated components. Cell 12 is held by supports 48 and 50 on top of balance 14. Soil sample 55 (in this preferred embodiment) is placed within cell 12 so that its entire cross section is exposed at opposite ends to end pieces 52 and 54, which are connected to tubing 16. The structure of cell 12 can be conventional as is known in the art. It can include two plates 56 and 58 to contain the sample in that orientation.

Temperature sensors 42 are installed through a stopper 60 into the interior of tubing 16 outside end pieces 52 and 54 of cell 12. Pressure transducers 44A and 44B are in communication with opposite end pieces 52 and 54. A pressure transducer 44C is placed along tubing 62 between transducers 44A and 44B. Transducers 44A and 44B therefore allow measurement of absolute pressure across sample 55. Transducer 44C measures relative pressure between ends of cell 12.

It is to be understood that tubing 16 is configured with respect to cell 12 so that balance 14 can measure the gravimetric weight of cell 12 and sample 55 (and tubing 62, sensors 44 and 42, stopper 60, and part of tubing 16). By previously knowing the weight of all these components without a sample 55 in cell 12, after placement of the sample 55 in cell 12, its weight can be derived.

c. General Discussion of Operation

System 10 can determine concurrently the relationships of water content, thermodynamic water potential, apparent permeability, and intrinsic permeability of soil sample 55. It is to be understood, however, that system 10 is also applicable to any porous material suffused with any fluid possessing a significant vapor pressure. Examples of such fluids are organic solvents and pesticides.

These physical and chemical properties, and relationships, include such things as water content - water potential relationship, and hysteresis in the relationship, intrinsic permeability (permeability corrected for slip-flow), permeability of multi-phase systems (for example, permeability of partially saturated media) and specific surface area.

Specific properties can be measured as follows:

1. Sample Geometry

This can be manually entered by visual description into software programming utilized by controller 46.

2. Water Content

May be determined gravimetrically by weighing sample 55 on electronic balance 14.

3. Water Potential

Measured with relative humidity sensor (capacitance type) in humidity and temperature measurement chamber 40.

4. Air Permeability

Pressure drop across sample 55 is measured and permeability is calculated from this measurement, from flow rate and temperature of air crossing sample, and from sample geometry.

Control of conditions at sample 55 are directed by controller 46. For example, moisture content or moisture potential is controlled by manipulating flow, pressure, and humidity of the air stream passing through sample 55 in chamber 12. Controller 46 actuates selected valves individually or concurrently to obtain the desired air flow path or direction through cell 12 and the physical conditions desired.

Controller 46 continuously monitors all sensors. The monitored information is used to control flow path, flow rate, humidity, and sample moisture content. Controller 46 also has memory means to store data and utilize the data to drive desired physical and chemical parameters.

d. Example of Operation

FIG. 1 shows system 10 configured for a sample desiccation (drying) mode. Tubing 16 is closed to atmosphere by de-energizing valves 32 and 34. Pump 18 is then instructed to create air flow through the circuit. Valve 28 is de-energized to bypass wetting flask 30. Valve 24, however, is energized to cause air flow through desiccator 26. Valve 20 is de-energized and valve 22 energized, so that the air flowing through desiccator 26 is directed into the right side of sample cell 12, exits the left side, and passes through valve 22, humidity and temperature measurement chamber 40, and back to pump 18. Air then flows from right to left across sample 55 and temperature and pressure sensors 42 and 44, as well as through a humidity and temperature sensor in measurement chamber 40. Moisture therefore can be removed from sample 55 and temperature, pressure, and humidity conditions measured.

e. Alternative Example of Operation

Humidification of sample 55 can be achieved by de-energizing valve 24, and energizing valve 28. Air is thereby diverted through wetting flask 30 (containing a free water surface), and bypassing desiccator 26.

f. Alternative Example of Operation

Absolute pressure within system 10 is adjusted by energizing valve 34 to pump air out of the system resulting in reduced pressure. Conversely, energization of valve 32 pumps air into the system resulting in increased pressure.

g. Summary of Valve Operation

Below is a table that summarizes the energy condition of each of valves 20, 22, 24, 28, 32, and 34, and indicates the effect on system 10. It is to be understood that symbol D=de-energized (closed), E=energized (open), and NR=not relevant (either energy status can occur and does not affect the process).

| SYSTEM CONDITION | VALVE 34 | VALVE 32 | VALVE 28 | VALVE 24 | VALVE 20 | VALVE 22 |
|---|---|---|---|---|---|---|
| FLOW R L | NR | NR | NR | NR | D | E |
| FLOW L R | NR | NR | NR | NR | E | D |
| DRY SAMPLE | D | D | D | E | NR | NR |
| WET SAMPLE | D | D | E | D | NR | NR |
| INCREASE PRESSURE | D | E | NR | NR | NR | NR |
| DECREASE PRESSURE | E | D | NR | NR | NR | NR |
| WEIGHT SAMPLE | D | D | D | D | NR | NR |
| EQUILIBRATE SYSTEM | D | D | D | D | NR | NR | h. Miscellaneous Operational Matters

The preferred embodiment allows a number of concurrent measurements to be controlled and accurately performed. Additionally, system 10 allows significant flexibility and advantages.

One such advantage is the ability to quickly reverse air flow through sample 55. This is done simply by altering the energy status of valves 20 and 22. According to one method of operation of the system 10 according to the invention, it is at times advantageous to periodically reverse air flow through sample 55. One aspect of such an operation is the physical advantage of causing periodic flucuations in pressure potential in the soil. Pressure flucuations in a compressible fluid (i.e., air or gas) cause compressive advection to occur in poorly connected (or dead-end) sample pores. Compression of air into these pores leads to enhanced mixing of local air with air passing through the sample. This enhancement overcomes diffusion-limited water movement, which results in achieving a more uniform water potential and water distribution within the sample in a much shorter time.

Another advantage is improved experimental precision. Pressure measuring devices (i.e., wheatstone bridge pressure transducers) almost invariably suffer drift after calibration. Reversing air flow direction reverses the air pressure ingredient. Therefore, any overestimate in pressure drop in one direction of air flow will result in equal underestimate of pressure drop when flow is measured in the reverse direction. By averaging these two values, drift is cancelled out and the results are improved in quality.

System 10 allows other operational procedures, including but not limited to:

i. Test Control Criteria

Controller 46, by monitoring system 10 with sensors, can automatically respond to changes in a sample's water potential, water content, or air permeability. Such changes can occur within a sample during a test. Software can allow a user to specify which soil property will be referenced in the system controls and how it will be used as a control criteria. For example, water content can be changed in various mass increments. At each increment the system will equilibrate the sample and then record permeability, water potential, water content, and temperature data before moving on to the next increment specified. Resolution of the increments is only limited by the resolution of sensors employed.

As a specific example, if a small sample 55 is being measured to derive a surface area, water content may be incremented in a small specified increment of 0.01 g (grams). Alternatively a large sample studied for air permeability may have a specified increment of 10 g.

j. Air Flow Rate

Air flow rate through sample 55 can be controlled by controlling the speed of pump 18. In the preferred embodiment, controller 46 uses a proportional 4-20 mA (millamp) signal to control pump speed. Speed can be controlled based either upon a set flow rate or a specified pressure drop across sample 55. When a control flow rate mode is chosen, the pump runs at a constant speed and the pressure drop created by the sample is recorded for permeability calculations. When a pressure drop is specified, the controller adjusts the pump speed, and feedback from a differential pressure measurement taken on the sample is used to increase or decrease the pump speed and dial in on the specified pressure drop.

k. Air Stream Humidity

By configuring the pump in a closed loop circuit, the user can set pumping duration in a given valve configuration before a final measurement of a sample's water content, water potential, or permeability is made. The humidity of the air stream traveling around the loop can be altered by diverting flow through the desiccator 26 or humidifier 30.

l. Equilibrium of the Sample and the System

Quick and accurate equilibrium of the sample and system can be achieved with the invention. Relative humidity is measured downstream of the sample. Equilibrium conditions must be obtained to derive useful data. To assure equilibrium, the user specifies a timed delay for the reversal of the flow direction through the sample. The reversal flow will offset the water potential gradient created within the sample, which is a consequence of unidirectional pressure drop. The user can specify a number of pairs of alternating flow direction measurements to be taken as the system approaches equilibrium. The system measures humidity in mass while changing the moisture condition of the sample.

m. Gas Slippage Measurements

An additional feature of the system is the ability to investigate gas slippage (Klinkenberg effect) in its relationship to air permeability at any chosen water potential or water content. The measurement of permeability at various absolute (system) pressures is recorded for intrinsic permeability analysis. This is accomplished by changing system air pressure by pumping up or down to user specified absolute pressures using valves 32 and 34 and pump 18. Air flow, pressure drop, absolute pressure, and temperature are recorded to determine intrinsic permeability. Sample geometry is entered at a startup menu for subsequent data processing. Pressures both above and below atmospheric are easily obtainable.

n. Miscellaneous

It will be appreciated that the present invention can take many forms and embodiments. The true essence and spirit of this invention are defined in the appended claims, and it is not intended that the embodiment of the invention presented herein should limit the scope thereof.

For example, the method of the invention may utilize parts of system 10 in FIG. 1, or different components. Still further, the apparatus of FIG. 1 may utilize different components.

Additional features or options can be utilized with the system. For example, as shown in FIG. 1, a heater 64 can be utilized with wetting flask 30 to heat water within wetting flask 30. Heaters can be utilized with other components in the system such as desiccator 26, or measurement chamber 40, for example. Different types of valves could be utilized.

What is claimed is:

1. An apparatus for measurement of a variety of physical and chemical properties and relationships in a porous material comprising:
   sample holding means for supporting and containing a sample of porous material in an air tight manner;
   first and second connection means in fluid communication with the sample holding means;
   weighing means for weighing a sample in the sample holding means;
   fluid circuit means in fluid communication with the first and second connection means;
   pump means for pumping air in the fluid circuit means;
   humidifying means in fluid communication with the fluid circuit means;
   dehumidifying means in fluid communication with the fluid circuit means;
   fluid flow valve means for controlling communication and noncommunication of the humidifying and dehumidifying means with the fluid circuit means;
   vent means for selectively venting the fluid circuit means to atmosphere; and
   so that measures related to hydraulic, pneumatic, physical, and chemical properties can be made concurrently, compared over time against one another, and used to derive parameters or characteristics based on the measures, and so that conditions related to hydraulic, pneumatic, physical, and chemical properties can be adjusted to analyze affect on and to create desired conditions relative to the sample.

2. The apparatus of claim 1 wherein the weighing means comprises a gravimetric balance means.

3. The apparatus of claim 1 wherein the fluid circuit means comprises conduit means for allowing fluid flow.

4. The apparatus of claim 1 wherein the pump means comprises a positive displacement pump.

5. The apparatus of claim 1 wherein the humidifying means comprises a container presenting a free water surface to air flowing within the fluid circuit means.

6. The apparatus of claim 1 wherein the dehumidifying means comprises a desiccator means.

7. The apparatus of claim 1 wherein the fluid flow valve means connect and disconnect the humidifier and dehumidifying means to the fluid circuit means.

8. The apparatus of claim 1 wherein the fluid flow valve means alter the direction of fluid flow through the sample holding means.

9. The apparatus of claim 1 wherein the vent means are positioned on opposite sides of the pump means, one vent means allowing air from atmosphere to enter the fluid circuit means to increase pressure in the circuit; one vent means allowing air to vent to atmosphere to reduce pressure in the fluid circuit means.

10. The apparatus of claim 1 further comprising control means for operating the valve means and vent means.

11. The apparatus of claim 1 further comprising control means for operating the pump means.

12. The apparatus of claim 1 further comprising control means for monitoring temperature and sensor means in the system.

13. The apparatus of claim 1 further comprising heating means associated with the system for heating at least a portion of the system.

14. The apparatus of claim 1 further comprising humidity measuring means in the fluid circuit means.

15. The apparatus of claim 14 further comprising temperature measuring means in the fluid circuit means.

16. The apparatus of claim 1 wherein the sample holding means comprises a sealed chamber having first and second ends generally corresponding with the first and second connection means.

17. The apparatus of claim 16 further comprising first and second temperature sensor means at each end of the chamber.

18. The apparatus of claim 16 further comprising pressure transducer means at each end of the chamber for measuring absolute pressure.

19. The apparatus of claim 18 further comprising a differential pressure transducer between the pressure transducers at each end of the chamber to measure relative pressure in the chamber.

20. A method of measuring physical and chemical properties in a porous material comprising:
    placing a porous sample in a container;
    adjusting air flow through the sample;
    adjusting humidity of the sample;
    measuring parameters related to the sample; and
    so that measures related to hydraulic, pneumatic, physical, and chemical properties can be made concurrently, compared over time against one another, and used to derive parameters or characteristics based on the measures, and so that conditions related to hydraulic, pneumatic, physical, and chemical properties can be adjusted to analyze effect on and to create desired conditions relative to the sample.

21. The method of claim 20 further comprising adjusting air flow in either direction through the sample.

22. The method of claim 20 wherein the humidity is adjusted by wetting air flowing through the sample.

23. The method of claim 20 wherein the humidity is adjusted by drying air flowing through the sample.

24. The method of claim 20 further comprising equaliberating air flow, humidity, and temperature of the sample.

25. The method of claim 20 further comprising the step of controlling fluid communication of humidity, dehumidity, and atmospheric pressure to the container holding the sample.

26. The method of claim 20 further comprising measuring temperature, humidity, and pressure in the sample.

27. The method of claim 20 further comprising calculating relationships between parameters related to the sample.

28. The method of claim 20 further comprising adjusting one of air flow or humidity through the sample according to an incremented amount.

29. The method of claim 20 wherein the parameters include, but are not limited to, temperature, pressure, weight, and air flow.

30. The method of claim 21 wherein the parameters include sample geometry.

31. The method of claim 20 further comprising the step of periodically reversing air flow through the sample.

32. The method of claim 31 wherein parameter measurements are taken after each reversal of air flow.

33. The method of claim 31 wherein the air flow reversal is instructed according to a specific time delay.

34. A method of concurrent determination of relationships of such parameters as water content, thermodynamic water potential, apparent permeability, and intrinsic permeability within a porous medium comprising:
    controlling simultaneously the following conditions at the porous medium;
        air flow through the medium;
        direction of air flow through the medium;
        humidity in the medium;
        pressure through the medium;
        temperature in the medium; measuring parameters associated with the conditions at the porous media; and
    so that measures related to hydraulic, pneumatic, physical, and chemical properties can be made concurrently, compared over time against one another, and used to derive parameters or characteristics based on the measures, and so that conditions related to hydraulic, pneumatic, physical, and chemical properties can be adjusted to analyze effect on and to create desired conditions relative to the sample.

35. The method of claim 34 further comprising incrementally varying at least one condition at the medium.

36. The method of claim 34 further comprising equilibrating the conditions in the medium.

37. The method of claim 36 further comprising altering the conditions at the medium and then measuring the parameters again at the medium.

* * * * *